United States Patent [19]

Birthwistle

[11] Patent Number: 5,246,694
[45] Date of Patent: * Sep. 21, 1993

[54] SHAMPOO COMPOSITION

[75] Inventor: David H. Birthwistle, Wirral, United Kingdom

[73] Assignee: Chesebrough-Pond's USA Co., Division of Conopco, Inc., Greenwich, Conn.

[*] Notice: The portion of the term of this patent subsequent to Feb. 4, 2009 has been disclaimed.

[21] Appl. No.: 733,506

[22] Filed: Jul. 22, 1991

[30] Foreign Application Priority Data

Jul. 23, 1990 [GB] United Kingdom ............... 9016100

[51] Int. Cl.$^5$ .............................................. A61K 7/06
[52] U.S. Cl. ........................................ 424/70; 424/71; 424/DIG. 2; 514/941
[58] Field of Search ................ 424/70, 71, DIG. 2; 106/287.15; 514/941

[56] References Cited

U.S. PATENT DOCUMENTS

| | | | |
|---|---|---|---|
| 3,964,500 | 6/1976 | Drakoff | 424/70 |
| 4,298,494 | 11/1981 | Parslow et al. | 424/70 |
| 4,364,837 | 12/1982 | Pader | 424/70 |
| 4,673,568 | 6/1987 | Grollier et al. | 424/70 |
| 4,788,001 | 11/1988 | Narula | 514/941 |
| 4,902,499 | 2/1990 | Bolish, Jr. et al. | 424/DIG. 2 |
| 5,085,857 | 2/1992 | Reid et al. | 424/70 |

FOREIGN PATENT DOCUMENTS

| | | |
|---|---|---|
| 0240350 | 10/1987 | European Pat. Off. . |
| 0285389 | 10/1988 | European Pat. Off. . |
| 0400976 | 12/1990 | European Pat. Off. . |
| 0432951 | 6/1991 | European Pat. Off. . |
| 61-161214 | 7/1986 | Japan . |
| 62-234012 | 10/1987 | Japan . |
| 2161172 | 1/1986 | United Kingdom . |

Primary Examiner—Thurman K. Page
Assistant Examiner—William E. Benston, Jr.
Attorney, Agent, or Firm—Milton L. Honig

[57] ABSTRACT

A shampoo composition comprises:
(a) a surfactant which is chosen from anionic, nonionic or amphoteric surfactants or mixtures thereof;
(b) an aqueous emulsion of a solution of highly viscous silicone in volatile solvent; and
(c) a cationic conditioning polymer which is a cationic derivative of guar gum;

wherein the average particle size of the highly viscous silicone in the composition is less than 2 μm in diameter.

4 Claims, No Drawings

SHAMPOO COMPOSITION

BACKGROUND OF THE INVENTION

The present invention relates to shampoo compositions, and more particularly to shampoo compositions containing highly viscous silicones which are preferably silicone resinsor siloxane gums, giving body to fine, limp hair and increasing the ability of hair to hold a style.

The property of hair known as "body" is a complex one, and can be interpreted as fullness or volume of the hair. It also embraces ease of styling and ability to hold a style. Fine hair often suffers from a lack of body and is found to be limp and unmanageable.

Other types of hair can benefit from an increased ease of styling and an increased ability to hold a style. Generally, this is achieved by application of film-forming materials to the hair, usually after shampooing and/or conditioning in the form of mousses, gels or sprays.

Silicone materials have been applied to the hair to give some conditioning benefit, see for example U.S. Pat. No. 3 964 500 and U.S. Pat. No.4 364 837. However, the silicones used are generally of relatively low viscosity since low viscosity silicones are more readily incorporated into shampoo compositions.

Highly viscous silicones have the ability to modify the condition and manageability of hair. Siloxane gums improve the combability, softness and condition of the hair and reduce its susceptibility to damage due to mechanical manipulation caused for example by brushing and styling. Silicone resins give body to fine, limp hair and increase the ability of hair to hold a style.

These highly viscous silicones are extremely difficult to incorporate into a shampoo product, because they cannot be dispersed to form droplets or an emulsion. To aid dispersion, the highly viscous silicones must be first dissolved in a volatile solvent in order that the viscosity be reduced. The solution of the highly viscous silicone may then be emulsified.

In JP 61/161214 (Shiseido), setting compositions comprising silicone resin and volatile silicone are disclosed. These compositions are delivered from both leave-on and rinse-off compositions containing volatile solvents which evaporate to leave the silicone resin on the hair.

EP 240 350 (Procter & Gamble) relates to compositions comprising a rigid silicone polymer and a volatile carrier.

The droplets of silicone polymer in volatile silicone, obtained by the process used in EP 240 350 are in general greater than 5 $\mu$m in diameter on average. Such relatively large particles are more difficult to suspend in a shampoo system, and can give rise to processing difficulties with the need for hot processing and high shear mixing.

Particles having an average diameter of less than 2 $\mu$m tend to remain suspended in a shampoo composition and are therefore rinsed from the hair. We have found however that by including a cationic derivative of guar gum in the shampoo composition, small particles, i.e. those having an average diameter of less than 2 $\mu$m, can be effectively deposited on the hair shaft.

BRIEF SUMMARY OF THE INVENTION

Accordingly the invention provides a shampoo composition comprising (a) a surfactant which is chosen from anionic, nonionic or amphoteric surfactants or mixtures thereof; (b) an aqueous emulsion of a solution of highly viscous silicone in volatile solvent; and (c) a cationic conditioning polymer which is a cationic derivative of guar gum; wherein the average particle size of the silicone resin in the composition is less than 2 $\mu$m in diameter.

DETAILED DESCRIPTION OF THE INVENTION

(a) Surfactant

The composition of the invention comprises a surfactant which is chosen from anionic, nonionic or amphoteric surfactants or mixtures thereof.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally containing from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other suitable nonionics include mono- or di-alkyl alkanolamides. Examples include coco mono- or di-ethanolamide and coco mono-isopropanolamide.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The surfactants are preferably present in the shampoo composition of the invention in an amount of from 2 to 40% by weight, and most preferably from 5 to 30% by weight.

(b) Emulsion

The shampoo composition according to the invention comprises an aqueous emulsion of a solution of highly viscous silicone in volatile solvent. This emulsion is prepared by first dissolving the highly viscous silicone in the volatile solvent, adding emulsifier and water, and mixing to form an emulsion. The highly viscous silicone is preferably chosen from silicone resin or siloxane gum or mixtures thereof.

The silicone resins suitable for use in the compositions of the invention are preferably oligomerous alkylpolysiloxanes, arylpolysiloxanes or alkylarylpolysiloxanes, composed of suitable combinations of $R_3SiO_{0.5}$ units, $R_2SiO$ units, $RSiO_{1.5}$ units and $SiO_2$ units. Their ratio is selected so that the resin has average formula $R_nSiO_{[(4-n)/2]}$ where R is $C_{1-6}$ alkyl or aryl and n is from 0.7 to 1.8.

Suitable resins form films when the volatile silicone solvent removed by evaporation. These films are hard and brittle at ambient temperature but soften upon being heated. For suitable resins the temperature at which softening begins is preferably greater than 30° C.

It is preferred that the silicone resin has an average molecular weight of from 500 to 10000.

Suitable examples of silicone resins useful in the compositions of the invention are Siliconharz MK (Wacker) and MQ resin (General Electric).

Siliconharz MK is a silsesquioxane resin. Resin MQ is prepared by reaction of trimethyl chlorosilane or hexamethyl disilane with silicic or polysilicic acid in the presence of a weak acid in solvent.

Suitable siloxane gums for use in the shampoo composition of the invention include high molecular weight alkylpolysiloxane, arylpolysiloxane and alkylarylpolysiloxane, having a viscosity greater than 100,000 centistokes (cSt), preferably greater than 500,000 cSt.

Examples of suitable siloxane gums include SE30 and SE76, available from General Electric. These gums are polydimethylsiloxane gums having viscosities of greater than one million centistokes.

The emulsion comprises particles of a solution of highly viscous silicone having an average diameter of less than 2 μm, preferably from 0.01 to 1 μm. The average particle size may be measured for example by a laser light scattering technique using a 2600D Particle Sizer from Malvern Instruments.

The highly viscous silicones are generally present in amounts of from 0.1 to 5% preferably from 0.3 to 1.5% by weight, based on the total shampoo composition.

The highly viscous silicone is dissolved in a volatile solvent. As used herein, the term "volatile" means that the material has a measurable vapour pressure.

The preferred solvents are those having a boiling point of from 99° C. to about 260° C. and have a solubility in water of less than about 0.1%. Solvents are preferably chosen from volatile silicone or volatile hydrocarbon.

The most preferred solvents are volatile silicones, which may be either cyclic or linear polydimethyl siloxanes. The number of silicone atoms in the cyclic silicones is 3 to 7, most preferably 4 or 5. The general formula for cyclic silicones is:

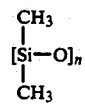

wherein n=3-7. Viscosities are generally less than 10 centipoise (cP) at 25° C.

Linear polydimethyl siloxanes useful in the invention generally have viscosities of about less than about 5cP at 25° C. The linear volatile silicones contain from about 3 to about 9 silicon atoms and have the general formula

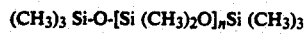

wherein n=1-7.

Silicones of the above described types are widely available, for example: from Dow Corning as 244, 245, 344, 345 and 200 fluids (cyclopolymethylsiloxane blends), 200/5 fluid (a very short linear polydimethylsiloxane) and 1401 fluid (a mixture of polydimethylsiloxanol gum and cyclopolymethylsiloxanes); from Union Carbide as TP503 fluid (an emulsion of polydimethylsiloxane gum in cyclopolymethylsiloxane) and Silicone 7202 and 7158; and from Stauffer Chemical as SWS-03314.

When the solvents are hydrocarbons, they may be for example, straight chain or branched chain alkyl and contain from 10 to 16 carbon atoms, preferably from 12 to 16 carbon atoms. Suitable examples are n-dodecane, permethylhydrocarbons 99A and 101A available from Presperse Inc.

The volatile solvent is generally present in an amount of from 0.1 to 10% preferably from 0.5 to 3%, by weight based on the total composition.

Any surfactant materials either alone or in admixture may be used as emulsifiers in the preparation of the silicone resin emulsions. Preferred emulsifiers include anionic emulsifiers such as alkylarylsulphonates e.g. sodium dodecylbenzene sulphonate, alkyl sulphates e.g. sodium lauryl sulphate, alkyl ether sulphates e.g. sodium lauryl ether sulphate nEO where n is from 1 to 20, alkylphenol ether sulphates e.g. octylphenol ether sulphate nEO where n is from 1 to 20, and sulphosuccinates e.g. sodium dioctylsulphosuccinate.

Also suitable are nonionic emulsifiers such as alkylphenol ethoxylates e.g. nonylphenol ethoxylate nEO, where n is from 1 to 50, alcohol ethoxylates e.g. lauryl alcohol nEO, where n is from 1 to 50, ester ethoxylates e.g. polyoxyethylene monostearate where the number of oxyethylene units is from 1 to 30.

The emulsion is preferably present in the shampoo composition in an amount of from 0.5 to 50% by weight, most preferably from 1 to 20% by weight.

The amount of emulsion present is an amount which is effective to give the desired quantity of silicone in the final composition.

(c) Cationic conditioning polymer

The shampoo composition of the invention also comprises a cationic conditioning polymer which is a cationic derivative of guar gum.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR 162 which is a high transparency, medium viscosity guar having a low degree of substitution.

The compositions of the invention may contain from about 0.01 to about 1% by weight of cationic conditioning polymer, preferably from about 0.04 to about 0.5% by weight.

Other ingredients

The compositions of the invention may also optionally further comprise a suspending agent which can act to suspend particulate matter in the shampoo composition.

Suitable suspending agents include gums such as xanthan gum, guar gums, polymers of acrylic acid which may optionally be cross-linked (e.g. Carbopol 940 or 1342 available from Goodrich), esters of ethylene glycol or esters of polyethylene glycol.

The shampoo composition of the invention may also further comprise minor amounts of other ingredients commonly found in shampoo compositions, such as antibacterial agents, antidandruff agents such as zinc pyridinethione or Octopirox, foam boosters, pearlescers, perfumes, dyes, colouring agents, preservatives, viscosity modifiers (e.g. thickening agents such as sodium chloride or ammonium chloride), proteins, polymers, buffering agents, polyols and other moisturising agents, and herb extracts.

Process for preparing the shampoo composition

The invention further comprises a process for preparing the shampoo composition described herein, which process comprises the steps of
(a) dissolving the highly viscous silicone in volatile solvent to form a solution;
(b) emulsifying the solution with water and an emulsifier to obtain an emulsion comprising particles of highly viscous silicone having an average diameter of less than 2μm;
(c) mixing the emulsion with a surfactant chosen from anionic, nonionic or amphoteric surfactants or mixtures thereof and a cationic conditioning polymer.

Other optional ingredients may be added to the composition at, or following step (c) above.

Use of the composition

The shampoo composition of the invention is applied in an amount of from 3 to 5ml to wet hair. The wet hair is worked to create a lather. The lather may be retained on the head for a short time before rinsing e.g. from 1 to 4 minutes, or may immediately be rinsed. The washing procedure may be repeated if required.

The invention is further directed to the use of at least 0.04% by weight of the total composition of a cationic derivative of guar gum, for depositing onto hair a particulate, highly viscous silicone in a shampoo composition, wherein the silicone is held in an emulsion, the composition otherwise comprising a major proportion of a surfactant.

The invention is further illustrated by the following Examples.

EXAMPLES

Example 1

A shampoo according to the invention having the following composition is prepared according to the invention by the process described herein:

|  | % wt |
| --- | --- |
| Sodium lauryl ether sulphate 2EO | 16.0 |
| Cocamidopropyl betaine | 2.0 |
| Carbomer 941[1] | 0.4 |

| | |
| --- | --- |
| Silicone emulsion[2] | 5.7 |
| Jaguar C13S | 0.1 |
| Perfume, preservative | qs |
| Water to | 100 |

[1]Carbomer 941 is the CTFA designation for a polymer of acrylic acid, cross-linked with a polyfunctional agent.
[2]the silicone emulsion comprises:

| | % wt |
| --- | --- |
| Siliconharz MK | 17.5 |
| Volatile silicone DC 344 | 17.5 |
| Lauryl alcohol ethoxylate 2EO/21EO* | 4.0 |
| Preservative | qs |
| Water to | 100 |

*a mixture of lauryl alcohol ethoxylate 2EO and lauryl alcohol ethoxylate 21EO.

The emulsion is prepared by mixing the ingredients at 70° C. using a high shear mixer, and then cooling.

The shampoo is prepared by mixing the ingredients together at ambient temperature, using a paddle stirrer.

EXAMPLE 2

A shampoo composition according to the invention is prepared according to the process described herein.

| | % wt |
| --- | --- |
| Sodium lauryl ether sulphate 3EO | 18.0 |
| Lauryl betaine | 2.0 |
| Carbomer 941 | 1.5 |
| Silicone emulsion[3] | 4.3 |
| Jaguar C17 | 0.06 |
| Perfume, preservative | qs |
| Water to | 100 |

[3]The silicone emulsion comprises:

| | % wt |
| --- | --- |
| Siliconharz MK | 15.0 |
| Permethyl hydrocarbon 101A | 20.0 |
| Lauryl alcohol ethoxylate 2EO/21EO | 4.0 |
| Preservative | qs |
| Water to | 100 |

EXAMPLE 3

A shampoo composition according to the invention is prepared according to the process described herein:

| | % wt |
| --- | --- |
| Ammonium lauryl sulphate | 12.0 |
| Lauryl betaine | 4.0 |
| Carbomer 941 | 1.5 |
| Silicone emulsion[4] | 10.0 |
| Jaguar C13S | 0.15 |
| Perfumes, preservative | qs |
| Water to | 100 |

[4]The silicone emulsion comprises:

| | % wt |
| --- | --- |
| SR545[5] | 15.0 |
| Volatile silicone DC200/5 | 20.0 |
| Lauryl alcohol ethoxylate 2EO/21EO | 4.0 |
| Preservative | 2.0 |
| Water to | 100 |

[5]SR545 is MQ resin from General Electric. It is supplied as a solution in toluene and the toluene is removed prior to use.

EXAMPLE 4

A shampoo composition according to the invention is prepared according to the process described herein:

| | % wt |
| --- | --- |

| | % |
|---|---|
| Sodium lauryl sulphate | 6 |
| Sodium lauryl ether sulphate 2EO | 8 |
| Lauryl dimethyl betaine | 2 |
| Carbomer 941 | 1.5 |
| Silicone emulsion[6] | 4 |
| Jaguar C15 | 0.2 |
| Perfume, preservative | qs |
| Water to | 100 |

[6]The silicone emulsion comprises:

| | %wt |
|---|---|
| SE 30 siloxane gum | 10 |
| Permethylhydrocarbon 99A | 40 |
| Lauryl alcohol ethoxylate 2EO/21EO | 4 |
| Preservative | qs |
| Water to | 100 |

EXAMPLE 5

A shampoo composition according to the invention is prepared according to the process described herein:

| | %wt |
|---|---|
| Ammonium lauryl ether sulphate 3EO | 14 |
| Cocoamidopropyl betaine | 4 |
| Carbopol 940 | 0.3 |
| Silicone emulsion[7] | 6 |
| Jaguar C13S | 0.25 |
| Perfume, preservative | qs |
| Water to | 100 |

[7]The silicone emulsion comprises:

| | %wt |
|---|---|
| SE76 siloxane gum | 7 |
| Volatile silicone DC 345 | 28 |
| Lauryl alcohol ethoxylate 2EO/21EO | 4 |
| Preservative | qs |
| Water to | 100 |

Further examples of shampoo compositions according to the present invention are given in Examples 6 to 35 below. All amounts are expressed in %wt, except where otherwise stated.

| Example | 6 | 7 | 8 | 9 | 10 | 11 | 12 |
|---|---|---|---|---|---|---|---|
| Sodium lauryl ether sulphate 2EO | 16 | 16 | 16 | 16 | 16 | 16 | 16 |
| Cocoamidopropyl betaine | 2 | 2 | 2 | 2 | 2 | 2 | 2 |
| Carbopol 940 | 0.4 | 0.4 | 0.4 | 0.4 | 0.4 | 0.4 | 0.4 |
| Jaguar C13S | 0.1 | 0.1 | 0.1 | 0.1 | 0.1 | 0.1 | 0.1 |
| Siliconharz K | 1 | 0.5 | 1.5 | 2.5 | — | — | — |
| DC 344 | 3 | 3.5 | 2.5 | 4.0 | 0.3 | 0.6 | 3.0 |
| SE 30 gum | — | — | — | — | 0.05 | 0.1 | 0.5 |
| Perfume, preservative | q.s. | | | | | | |
| Sodium chloride | 3 | 4 | 3 | 4 | 1.5 | 2.0 | 4.0 |
| Water to | 100 | | | | | | |

| Example | 13 | 14 | 15 |
|---|---|---|---|
| Ammonium lauryl sulphate | 12 | 12 | 12 |
| Lauryl dimethyl betaine | 2 | 2 | 2 |
| Carbopol 1342 | 0.4 | 0.4 | 0.4 |
| Jaguar C13S | 0.5 | 0.5 | 0.5 |
| SR 545 | 1.5 | — | — |
| SE 76 gum | — | 0.25 | 0.75 |
| DC 345 | 2.5 | 1.5 | 3.0 |
| Perfume, preservative | q.s. | | |
| Ammonium chloride | 3 | 2.5 | 4.0 |
| Water to | 100 | | |

| Example | 16 | 17 | 18 | 19 |
|---|---|---|---|---|
| Sodium lauryl sulphate | 10 | 10 | 10 | 10 |
| Coco diethanolamide | 2 | 2 | 2 | 2 |
| Carbopol 1342 | 0.5 | 0.5 | 0.5 | 0.5 |
| Jaguar C17 | 0.5 | 0.5 | 0.5 | 0.5 |
| SR 545 | 1 | — | — | — |
| Siliconharz MK | — | 1.2 | — | — |
| DC 1401 | — | — | 1 | — |
| TP 503 | — | — | — | 5 |
| Polydimethylsiloxane (2 cSt) | 2 | — | — | — |
| DC 244 | — | 2.8 | — | — |
| Perfume, etc | q.s. | | | |
| Sodium chloride | 2 | 4 | 2 | 4 |
| Water to | 100 | | | |

| Example | 20 | 21 | 22 | 23 | 24 | 25 |
|---|---|---|---|---|---|---|
| Sodium lauryl ether sulphate 3EO | 14 | 14 | 14 | 14 | 14 | 14 |
| Lauryl dimethyl betaine | 3 | 3 | 3 | 3 | 3 | 3 |
| Carbopol 940 | 0.4 | 0.4 | 0.4 | 0.4 | 0.4 | 0.4 |
| Jaguar C13S | 0.2 | — | — | 0.3 | — | — |
| Jaguar C162 | — | 0.3 | — | — | 0.5 | — |
| Jaguar C17 | — | — | 0.3 | — | — | 0.1 |
| Siliconharz MK | 0.8 | 0.8 | 0.8 | — | — | — |
| SE 30 gum | — | — | — | 0.25 | 0.25 | 0.25 |
| DC 245 | 2.2 | 2.2 | 2.2 | 1.25 | 1.25 | 1.25 |
| Perfume, etc | q.s. | | | | | |
| Sodium chloride | 3.5 | 3.5 | 3.5 | 2.5 | 2.5 | 2.5 |
| Water to | 100 | | | | | |

| Example | 26 | 27 | 28 | 29 | 30 | 31 |
|---|---|---|---|---|---|---|
| Sodium lauryl ether sulphate 2EO | 15 | 15 | 15 | 15 | 15 | 15 |
| Lauryl dimethylbetaine | 3 | 3 | 3 | 3 | 3 | 3 |
| Jaguar C13S | 0.2 | 0.2 | 0.2 | 0.2 | 0.2 | 0.2 |
| Carbopol 940 | 0.4 | 0.4 | 0.4 | 0.4 | 0.4 | 0.4 |
| Siliconharz MK | 1 | 1 | 1 | 2 | 2 | 2 |
| SE 30 gum | 0.1 | 0.25 | 0.4 | 0.25 | 0.4 | 0.8 |
| DC 244 | 2 | 2.5 | 3 | 3.5 | 4 | 5 |
| Perfume etc | q.s. | | | | | |
| Sodium chloride | 2.5 | 3 | 3.5 | 4 | 4 | 5 |
| Water to | 100 | | | | | |

| Example | 32 | 33 | 34 | 35 |
|---|---|---|---|---|
| Sodium lauryl ether sulphate 3EO | 14 | 14 | 14 | 14 |
| Cocoamidopropyl betaine | 4 | 4 | 4 | 4 |
| Carbopol 1342 | 0.4 | 0.4 | 0.4 | 0.4 |
| Jaguar C17 | 0.15 | 0.15 | 0.15 | 0.15 |
| SR 545 | 0.8 | 0.8 | 0.8 | 0.8 |
| SE 76 gum | 0.1 | 0.3 | — | — |
| SE 30 gum | — | — | 0.1 | 0.3 |
| DC 345 | 2.0 | 2.5 | 2.0 | 2.5 |
| Perfume etc | q.s. | | | |
| Sodium chloride | 3.0 | 3.5 | 3.0 | 3.5 |
| Water to | 100 | | | |

I claim:
1. A shampoo composition comprising:
   (a) from 2 to 40% of a surfactant which is selected from the group consisting of anionic, nonionic, amphoteric surfactants and mixtures thereof;
   (b) from 0.5 to 50% of an aqueous emulsion of a solution of highly viscous silicone in volatile solvent, the highly viscous silicone being present in amounts of from 0.01 to 5% based on the total shampoo composition and being selected from the group consisting of silicone resin, siloxane gum and mixtures thereof, the volatile solvent being selected from the group consisting of volatile silicone and volatile hydrocarbon; and
   (c) from about 0.01 to about 1% of a cationic conditioning polymer which is guar hydroxypropyl trimonium chloride;
wherein the average particle size of the highly viscous silicone in the composition is from 0.01 to 1 μm in diameter.

2. A shampoo composition as claimed in claim 1 wherein the volatile silicone is selected from the group consisting of octamethyl cyclotetrasiloxane and decamethyl cyclopentasiloxane.

3. A shampoo composition as claimed in claim 1 which further comprises a suspending agent.

4. A process for preparing a shampoo composition according to claim 1 which comprises the steps of:
   (a) dissolving a highly viscous silicone in volatile solvent to form a solution, the highly viscous silicone being selected from the group consisting of silicone resin, siloxane gum and mixtures thereof, the volatile solvent being selected from the group consisting of volatile silicone and volatile hydrocarbon;
   (b) emulsifying the solution with water and an emulsifier to obtain an emulsion comprising particles of the highly viscous silicone having an average diameter of from 0.01 to 1 μm; and
   (c) mixing the emulsion with a surfactant selected from the group consisting of anionic, nonionic, amphoteric surfactants and mixtures thereof and a cationic conditioning polymer which is guar hydroxypropyl trimonium chloride.

* * * * *

UNITED STATES PATENT AND TRADEMARK OFFICE
CERTIFICATE OF CORRECTION

PATENT NO. : 5,246,694
DATED : September 21, 1993
INVENTOR(S) : David H. Birtwistle It is certified that error appears in the above-indentified patent and that said Letters Patent is hereby corrected as shown below:

On the title page, Item [75]:
Inventor's Name: "Birthwistle" should read -- Birtwistle --.

Signed and Sealed this

Third Day of May, 1994

Attest:

BRUCE LEHMAN

*Attesting Officer*     *Commissioner of Patents and Trademarks*